(12) United States Patent
Bedingfield et al.

(10) Patent No.: US 8,027,572 B2
(45) Date of Patent: Sep. 27, 2011

(54) DIALYSIS MACHINE HAVING MULTIPLE LINE VOLTAGE HEATER

(75) Inventors: John Bedingfield, Largo, FL (US);
 Brian Lauman, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 831 days.

(21) Appl. No.: 12/035,991

(22) Filed: Feb. 22, 2008

(65) Prior Publication Data

US 2009/0213521 A1 Aug. 27, 2009

(51) Int. Cl.
 *H05B 3/60* (2006.01)
(52) U.S. Cl. ........... 392/315; 604/29; 361/194; 361/160
(58) Field of Classification Search .................. None
 See application file for complete search history.

(56) References Cited

U.S. PATENT DOCUMENTS

| | | |
|---|---|---|
| 4,239,978 A | 12/1980 | Kofink |
| 4,267,430 A | 5/1981 | Downey |
| 4,360,338 A | 11/1982 | Katchka |
| 4,654,538 A | 3/1987 | Lethellier |
| 4,744,747 A | 5/1988 | Kawamura et al. |
| 4,780,805 A | 10/1988 | Chewuk et al. |
| 4,788,415 A | 11/1988 | Whipple, Jr. |
| 4,823,825 A | 4/1989 | Buechl |
| 4,843,301 A | 6/1989 | Belanger |
| 4,908,496 A | 3/1990 | Higgins |
| 5,097,402 A | 3/1992 | Kritz et al. |
| 5,153,805 A | 10/1992 | Tennant et al. |
| 5,194,718 A | 3/1993 | Reiser et al. |
| 5,270,519 A | 12/1993 | Higgins |
| 5,637,786 A | 6/1997 | Weber et al. |
| 5,825,974 A | 10/1998 | Hutton et al. |
| 5,908,571 A | 6/1999 | Scott |
| 6,031,210 A | 2/2000 | Wonka |
| 6,034,358 A | 3/2000 | Higgins |
| 6,233,397 B1 | 5/2001 | Offir |
| 6,522,844 B2 | 2/2003 | Yamane et al. |
| 6,614,008 B2 | 9/2003 | Tidrick |
| 6,772,640 B1 | 8/2004 | Quigley et al. |
| 7,230,209 B2 | 6/2007 | Sterling |
| 2005/0105239 A1 | 5/2005 | Satoh et al. |

(Continued)

FOREIGN PATENT DOCUMENTS

DE 35 43 017 2/1987

(Continued)

OTHER PUBLICATIONS

Baxter Healthcare Corporation, "HomeChoice, HomeChoice PRO Automated PD Systems," 2001, USA.

(Continued)

*Primary Examiner* — Thor S Campbell
(74) *Attorney, Agent, or Firm* — K&L Gates LLP

(57) ABSTRACT

A dialysis machine having a multiple line voltage heater includes first and second heater elements, first and second switching devices connected electrically to the first and second heating elements, first and second power lines, and a control element configured to provide a first switching device state in which power at a first voltage is supplied via the first and second power lines to both first and second heater elements via both first and second switching devices and a second switching device state in which power at a second voltage is supplied via the first and second power lines to the first heater element only via the first switching device.

20 Claims, 11 Drawing Sheets

U.S. PATENT DOCUMENTS

2008/0058712 A1  3/2008  Plahey

FOREIGN PATENT DOCUMENTS

| DE | 38 17 770 | 11/1989 |
|----|-----------|---------|
| DE | 42 42 432 | 6/1994  |
| EP | 0 563 760 | 10/1993 |
| EP | 1 830 370 | 9/2007  |

OTHER PUBLICATIONS

Baxter Healthcare Corporation, "HomeChoice, HomeChoice PRO Automated PD Systems," 2003, USA.

Baxter Healthcare (Asia) Pte Ltd, "HomeChoice™, Automated PD System," 1998, USA.

Section 12, Technical Specifications, copyright 1994-2003, Baxter Healthcare Corporation.

Section 12, Technical Specifications, copyright 1999, Baxter Healthcare Corporation.

HomeChoice System, HomeChoice Pro System, Patient At-Home guide, Section 1, copyright 1994-2003, Baxter Healthcare Corporation.

U.S. Appl. No. 12/036,003, filed Feb. 22, 2008, John Bedingfield et al.

U.S. Appl. No. 12/035,998, filed Feb. 22, 2008, John Bedingfield et al.

FIG. 9

| | Data at min. hold duty cycle | | | | Coil Data at 100% duty cycle* | | | | Ratio hold duty cycle to ohms | Case Temp | Calculated Coil Temp |
|---|---|---|---|---|---|---|---|---|---|---|---|
| Min hold duty cycle | Coil Amp | Coil Volts | Coil Watt | Coil Ohms | Amps | Volts | Watts | Ohms | | | |
| 17.97 | 0.181 | 2.74 | 0.49594 | 15.13812 | 1.073 | 19 | 20.387 | 17.70736 | 1.014832 | 22.3 | 22.3 |
| 18 | 0.178 | 2.76 | 0.49128 | 15.50562 | 1.031 | 19 | 19589 | 18.42871 | 0.976737 | 24 | 32.66569 |
| 19 | 0.176 | 2.93 | 0.51568 | 16.64773 | 0.985 | 19.03 | 1874455 | 19.3198 | 0.983447 | 29 | 45.47051 |
| 19.8 | 0.18 | 3.07 | 0.5526 | 17.05556 | 0.96 | 19.01 | 18.2496 | 19.80208 | 0.999895 | 32 | 52.40092 |
| 20 | 0.178 | 3.1 | 0.5518 | 17.41573 | 0.96 | 19.02 | 18.2592 | 19.8125 | 1.009464 | | 52.5506 |
| 22.4 | 0.184 | 4.05 | 0.7452 | 22.01087 | 0.869 | 19.05 | 16.55445 | 21.92175 | 1.021816 | 52 | 82.86029 |
| 22.6 | 0.181 | 4.09 | 0.74029 | 22.59669 | 0.874 | 19.06 | 16.65844 | 21.80778 | 1.036327 | 55 | 81.22257 |
| 22.86 | 0.19 | 4.14 | 0.7866 | 21.78947 | 0.872 | 19.06 | 16.62032 | 21.8578 | 1.045851 | 60 | 81.94132 |
| 23.7 | 0.192 | 4.29 | 0.82368 | 22.34375 | 0.843 | 19.08 | 16.08444 | 22.63345 | 1.047123 | 62 | 93.08738 |
| 24.17 | 0.196 | 4.4 | 0.8624 | 22.44898 | 0.831 | 19.12 | 15.88872 | 23.00842 | 1.050485 | 67 | 98.47569 |
| 24.5 | 0.196 | 4.46 | 0.87416 | 22.7551 | 0.829 | 19.12 | 15.85048 | 23.06393 | 1.062265 | 70 | 99.27334 |
| 25.16 | 0.198 | 4.58 | 0.90684 | 23.13131 | 0.812 | 19.07 | 15.48484 | 23.48522 | 1.071312 | 73 | 105.3272 |

DIALYSIS MACHINE HAVING MULTIPLE LINE VOLTAGE HEATER

CROSS REFERENCE TO RELATED APPLICATIONS

This patent application shares a common specification and drawings with U.S. patent application Ser. Nos. 12/036,003 and 12/035,998.

BACKGROUND

The examples discussed below relate generally to medical fluid delivery. More particularly, the examples disclose systems, methods and apparatuses for dialysis such as hemodialysis ("HD") automated peritoneal dialysis ("APD").

Due to various causes, a person's renal system can fail. Renal failure produces several physiological derangements. The balance of water and minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is peritoneal dialysis, which infuses a dialysis solution, also called dialysate, into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter and into the patient's peritoneal cavity, allowing for the dialysate to dwell within the cavity and for the transfer of waste, toxins and excess water to take place. The source can be multiple sterile dialysate solution bags.

APD machines pump spent dialysate from the peritoneal cavity, through the catheter, to the drain. As with the manual process, several drain, fill and dwell cycles occur during dialysis. A "last fill" occurs at the end of APD, which remains in the peritoneal cavity of the patient until the next treatment.

APD machines require power for operation. One issue associated with powering APD machines is adapting the machine for use in countries having different operating voltages. In particular, fluid heating is effected because different operating voltages can cause the heater to heat differently. Another issue associated with powering APD machines is coping with power loss situations. A battery back-up can be provided. Here, it is desirable for the machine to draw power efficiently to preserve battery life. The systems below attempt to addresses the above-mentioned issues.

SUMMARY

The present medical fluid treatment systems rely on battery power (or other depletable power source) for back-up operation. The systems attempt to minimize power consumption to maximize operational time when running on the back-up battery. The systems in one embodiment drive pinch valves using solenoids. Here, the systems, e.g., via pulse-width-modulation "PWM" control, switch the power supplied to the solenoid between two levels, a first level to actuate the solenoid and a second reduced power level to hold the solenoid in the actuated state. The minimum required hold power can be, e.g., one thirtieth of the power required to actuate the solenoid. The bi-level control provides significant power savings, especially if the solenoid spends significant time in the hold state. The use of PWM control provides a relatively simple and efficient method to vary the power supplied to the solenoid between actuate and hold states. Even so, PWM alone (without feedback) is limited to, e.g., one tenth of the actuation power because a sufficient margin of safety is needed to ensure correct solenoid function under all conditions of use, including temperature, vibration, unit-to-unit variation, etc.

In one embodiment, the present disclosure provides a solenoid system, which uses solenoid coil current sensing to detect solenoid armature motion, and provides feedback to a solenoid control circuit, which uses the feedback information to reduce power dissipation and operating noise in a solenoid. Such circuit improves solenoid reliability, reduces the necessary margin of safety and provides solenoid failure detection. Here, the circuit senses the current level released by the solenoid when commanded to do so. That current level plus an increment, e.g., 10% is then set to be the hold current level for the next solenoid actuate/hold cycle. Here, the hold current is optimized based on real time or near real time data for each solenoid of the system. In that regard, it is contemplated to optimize each solenoid independently using the system and method of the first primary embodiment.

In another primary embodiment, the present disclosure provides a system that uses solenoid coil voltage and current sensing along with knowledge of coil resistance at a known temperature to derive coil temperature. The derived temperature is compared to a threshold temperature and if the derived temperature is above the threshold, the system removes power from the solenoid to protect the solenoid from overheating. When the derived temperature is below the threshold, the system uses the temperature in a solenoid control algorithm to perform solenoid drive temperature compensation.

The solenoid control algorithm uses the solenoid current feedback together with the derived solenoid coil temperature to improve power efficiency.

The improved power efficiency results from the reduction of the required safety margin to a lower level. Indeed, testing of this second preliminary embodiment allowed the holding power to be reduced by a factor of about 1.8 when the coil temperature was at 22.3° C., relative to the holding power required at a coil temperature of 105° C. At coil temperatures below 22.3° C., the required holding power will be even less. The improved efficiency is due to an elimination of the temperature related safety margin that would otherwise be required if coil temperature were not known.

The system of the second primary embodiment also reduces heat generation in the solenoid, which improves reliability and provides a means to monitor solenoid coil temperature and to shut down the solenoid in the event of excess temperature which could damage or cause malfunction of the solenoid. One failure mode associated with excess heat occurs due to thermal expansion which causes the valve to stick in an open (actuated) position. In one application, namely, a gravity-based dialysis machine, a stuck open valve presents a potential hazard of dialysate overfill to the patient. This second primary embodiment mitigates that hazard by reducing the hold power and the resultant heat generated within the solenoid, making excessive coil temperatures less likely to occur. The system also provides a way to place the solenoid in a safe (released state) if the solenoid temperature approaches the temperature at which sticking can occur.

In a further primary embodiment of the present disclosure, a system for fluid heating, e.g., the heating of dialysate bags as part of an APD machine, is provided. The heating system is relatively low cost and operates on any alternating current ("AC") line voltage ranging from, e.g., 94 VAC to 264 VAC and at a 47 to 63 Hz line frequency. The heating system uses a microcontroller that communicates with the rest of the APD system via an optically-isolated bi-directional serial bus. The heating sub-system is configured to detect AC line voltage automatically in one embodiment and configure itself accordingly. The heating sub-system in one embodiment uses two resistive heating elements of different resistances to minimize the number of switching components, which reduces cost and eliminates several failure modes.

It is, therefore, an advantage of the present disclosure to provide a solenoid actuation system operable, for example, to occlude and open medical fluid pinch valves that provides relatively low cost verification of pinch valve actuation without requiring a position sensor.

It is another advantage of the present disclosure to provide a solenoid actuation system operable, for example, to occlude and open medical fluid pinch valves that reduces armature hold power. Such armature hold power is important in battery operated systems.

It is a further advantage of the present disclosure to provide a solenoid actuation system operable, for example, to occlude and open medical fluid pinch valves that reduces heat generation due to reduced power dissipation.

It is still another advantage of the present disclosure to provide a solenoid actuation system operable, for example, to occlude and open medical fluid pinch valves that reduces solenoid operating noise.

It is still a further advantage of the present disclosure to provide a solenoid actuation system operable, for example, to occlude and open medical fluid pinch valves that improves solenoid reliability.

It is yet a further advantage of the present disclosure to provide a dual supply line voltage fluid heating system that detects an alternating current ("AC") line voltage and automatically configures the system for operation on the voltage detected.

It is still a further advantage of the present disclosure to provide a dual supply line voltage fluid heating system that can include precision zero cross detection for reduced EMI.

It is yet another advantage of the present disclosure to provide a dual supply line voltage fluid heating system that lowers cost and increases reliability via the elimination of a switching element.

It is still another advantage of the present disclosure to provide a dual supply line voltage fluid heating system that improves heater efficiency by heat-sinking switching elements to the heater plate and eliminating a separate heat sink for the switching elements.

It is yet a further advantage of the present disclosure to provide a dual supply line voltage fluid heating system that reduces the danger of shorting the AC line if the switching elements are configured incorrectly.

Additional features and advantages are described herein, and will be apparent from, the following Detailed Description and the figures.

BRIEF DESCRIPTION OF THE FIGURES

FIG. 9 is a compilation of data further illustrating certain hold current versus coil temperature concepts of the system and method of FIGS. 7 and 8.

DETAILED DESCRIPTION

Solenoid Control System with Reduced Hold Current

Figure 1:
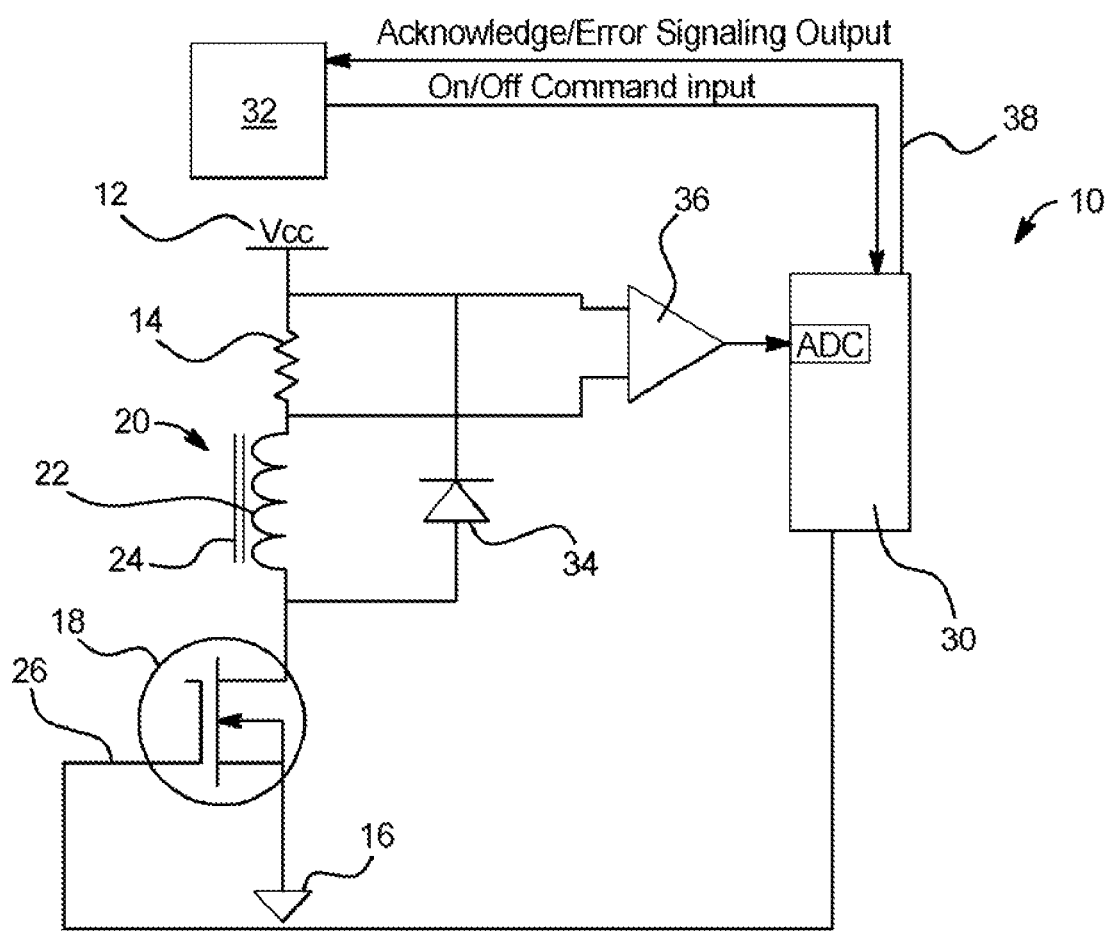
FIG. 1 is a schematic diagram illustrating one embodiment of a solenoid actuation system of the present disclosure.

Referring now to the drawings and in particular to FIG. 1, system 10 illustrates one apparatus and method for efficiently controlling a solenoid 20 having a solenoid coil 22 and an armature 24. One particularly well-suited application for system 10 is a medical fluid system, such as a peritoneal or hemodialysis system. Here, solenoid 20 is used to occlude a piece of tubing at a desired or programmed time within a valve control sequence for the dialysis machine. Solenoid 20 can be of a type in which a spring pushes armature 24 closed when coil 22 is not energized. The valve or tubing is thereby closed when no power is delivered to the solenoid. The valve or tubing is opened when power is delivered to solenoid 20. This configuration of solenoid 20 is advantageous in one respect because it fails in a closed state upon a power loss, which is generally desired. Alternatively, solenoid 20 is of a type in which the spring pulls armature 24 away from the tubing in a non-energized state. Here when energized, coil 22 overcomes the spring force and pushes armature 24 towards the tube or valve to close same. It may be advantageous to use this type of valve in a situation where the valve is programmed to be opened or non-energized for the majority of a treatment.

It should be appreciated that while dialysis is one sample application for system 10, system 10 can be applied to other medical fluid delivery systems using tubing or systems that are otherwise amenable to electromechanical solenoid valve control. System 10 includes a power supply 12, which can be a direct current ("DC") power supply (labeled Vcc). Power supply 12 provides the operating power to the various circuits of system 10.

System 10 includes a resistor 14 placed between power supply 12 and solenoid 20. Any current from supply 12 that passes through coil 22 of solenoid 20 also passes through resistor 14. It is desirable to keep power losses to a minimum. Therefore, in one preferred embodiment, a resistance of resistor 14 is selected to be low, on the order of milliohms, which reduces the power loss within resistor 14. In another preferred embodiment, resistor 14 is the resistance inherent in the circuit interconnect, e.g., printed circuit board trace or cable wiring. Such arrangement has the advantage of not adding an additional power dissipating element and eliminating the cost of an extra resistor.

System 10 further includes a switching device 18, which selectively allows current from power source 12 to flow through coil 22 and switch 18 to ground 16. In the illustrated embodiment, switching device 18 is a field affect transistor ("FET"). FET 18 includes a gate 26, which receives a control signal from a control element 30. Control element 30 can, for example, be a microprocessor storing a control algorithm that is operable with a memory also provided at control element 30. The control algorithm of control element 30 depends upon the specific requirements of the particular application in which system 10 is implemented.

As discussed, system 10 in one embodiment operates solenoid 20 to control a pinch valve that opens or occludes a pliable plastic tube in either the energized or non-energized state. The control algorithm is alternatively configured when system 10 is used in a different application. System 10 in one embodiment is replicated for each solenoid 20. For example, for a dialysis system using three pinch valves, three separate systems 10 are provided. It is contemplated to use a single control element 30 for multiple solenoids 20. Alternatively, a separate control element 30 is provided for each system 10.

Control element 30 (including multiple solenoid control elements 30) receives an on/off command input from a master or supervisory controller 32. In an embodiment, the chain of command begins at supervisory controller 32, or perhaps even at a higher level controller, e.g., a central processing unit overseeing supervising controller 32, which in turn commands control element 30 to either supply or not supply power to gate 26 of FET 18. Control element 30 is also configured to send an acknowledge/error signaling output 38 to communicate with the main or higher level processor.

In an alternative embodiment, control element 30 is the main system control processor or central processing unit. Main processor 30 receives an on/off command from another process running on the same control processor 30 (or even a delegate processor). Here, main processor 30 would send acknowledge/error signaling output 38 to another process running on the same processor 30 or on a delegate processor. In any case, control element 30 contains the herein described pinch valve control algorithm in one preferred embodiment.

As discussed, ground 16 provides a current return path to power supply 12. When switching element or FET 18 is switched off, current ceases to flow through switching device 18 and back to power supply 12. However, due to an inductance of coil 22 and a recirculation diode 34, current continues to circulate for a short time, decaying exponentially and asymptotically approaching zero (in one embodiment for more than 100 milliseconds) through resistor 14, coil 22 of solenoid 20 and diode 34. In operation, switching element 18 is likely to be switched on and off at a rapid rate (e.g., in a kHz range). The above-mentioned current through coil 22 of solenoid 20 and resistor 14 is maintained at an average level that is proportional to a duty cycle of a pulse-width-modulated ("PWM") waveform that control element 30 supplies to gate 26 of FET 18.

The current flowing through coil 22 and resistor 14 produces a voltage across resistor 14, which is proportional to the current. System 10 includes an amplifier 36, which in one embodiment is a differential amplifier. Amplifier 36 provides an input to an analog to digital converter ("ADC"), which in one embodiment is located within control element 30. Because the resistance of resistor 14 is low in one embodiment, the voltage across it is also low and amplifier 36 is needed to amplify the voltage to a level compatible with the input range of the ADC of control element 30. Amplifier 36 also converts the differential voltage signal across resistor 14 (produced because signal is not referenced to ground) at the input of amplifier 36 to a ground referenced voltage, which control element 30 needs in one embodiment. Although not illustrated, an analog filter can be provided between amplifier 36 and the ADC of control element 30 to further condition the signal for the ADC of element 30. In operation, as current through coil 22 increases, the voltage across resistor 14 increases proportionally as does the digital representation produced by the ADC of this voltage.

Figure 2:
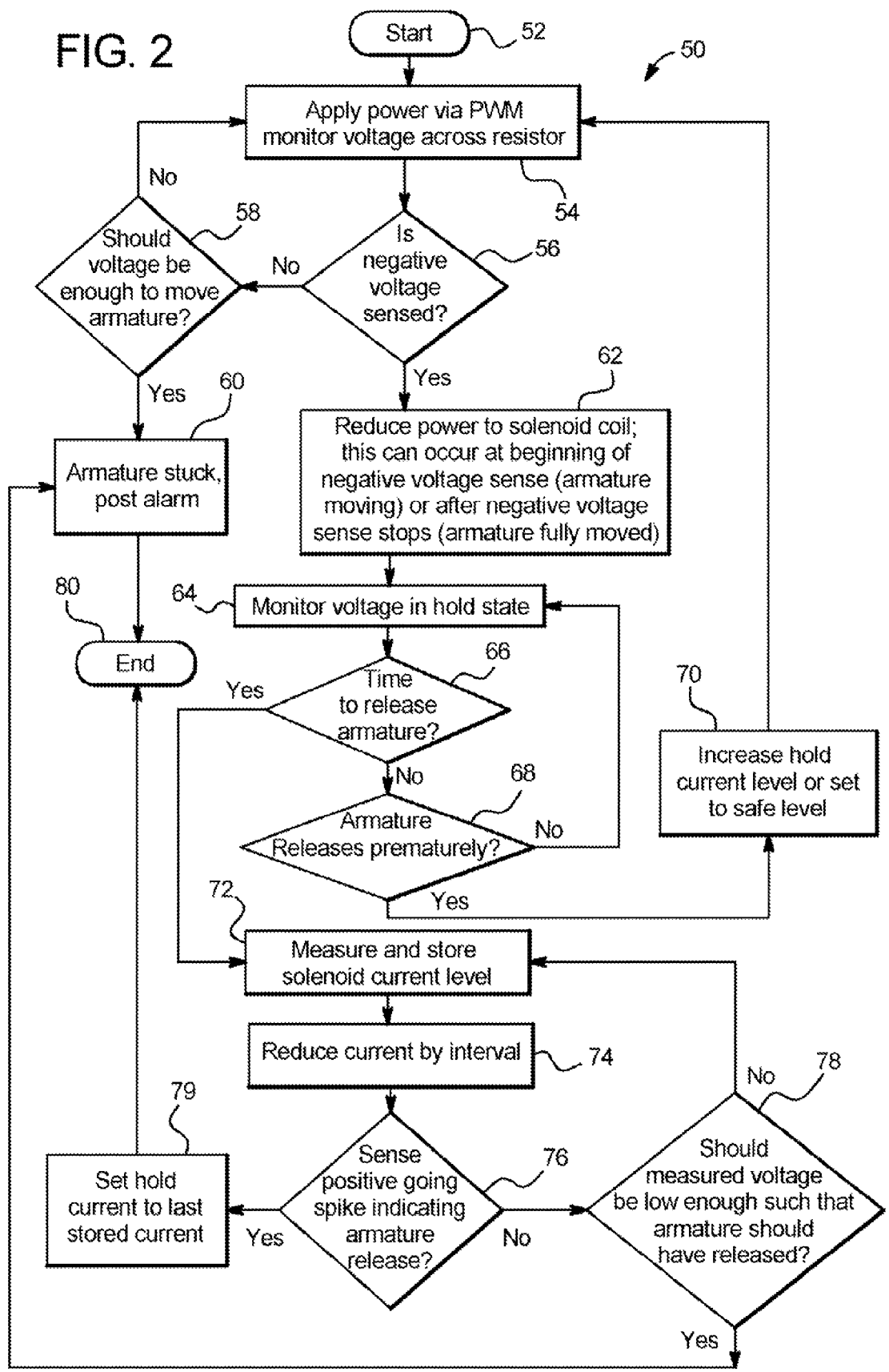
FIG. 2 is a logic flow diagram illustrating one embodiment of a method of operating the system of FIG. 1.

Referring now to FIG. 2, method 50 illustrates one method for controlling power from supply 12 to solenoid 20 in an efficient manner. Upon starting method 50 at oval 52, supervisory controller 32 in FIG. 1 commands control element 30 to actuate solenoid 20, e.g., via PWM. Control element 30 in one embodiment applies full voltage upon start up, i.e., PWM signal at 100% duty cycle is applied. Even so, due to solenoid coil inductance, the current ramps up slowly relative to the voltage and the sample rate of the ADC. For example, current can have a rise time of >100 ms with a voltage rise time of 50 nanoseconds. With an ADC sample rate of, e.g., 10,000 samples per second, the current rise can be digitized into about one-thousand samples. With the relatively slow current rise, control element 30 is able to readily spot a negative-going spike e.g., ~25 millisecond spike width or ~250 ADC samples) and reduce the PWM duty cycle which will proportionally reduce the hold current level as discussed below.

As mentioned, when power from supply 12 is applied initially, the current rise across resistor 14 due the inductance of coil 22 does not jump instantaneously but instead ramps up exponentially (asymptotically approaching steady state) over a period of milliseconds. At block 54, element 30 monitors the corresponding voltage increase across resistor 14 via amplifier 36. At block 56, method 50 looks to see if the current across resistor 14 has risen to a point at which armature 24 begins to move. When armature 24 begins to move, the armature induces a momentary negative-going current spike in solenoid coil 22, which control element 30 detects via amplifier 36. Control element 30 is programmed to know that the negative-going spike in current indicates that armature 24 of solenoid 20 has began to move. The negative-going current duration is approximately equal to the duration of armature 24 movement (e.g. ~25 milliseconds). Stated alternatively, the duration of movement of armature 24 is equal to the duration of the decrease in rate of current rise (compared to the rate of rise that a stuck armature solenoid would exhibit).

If the negative-going voltage spike is not sensed, as determined in connection with diamond 56, control element 30 determines whether the particular voltage level sensed across resistor 14 should have been enough to move armature 24, as determined in connection with diamond 58. That is, based on historical data or a predetermined voltage level, if it is expected that a particular voltage level for solenoid 20 should have actuated armature 24, but the negative-going spike has not been detected, then control element 30 in method 50 determines that armature 24 is stuck and posts a solenoid failure-to-actuate (valve stuck closed) alarm via acknowledge/error signaling output 38, as seen in connection with block 60. Method 50 then ends as seen at oval 80.

In an alternative embodiment (not illustrated), control element 30 at block 54 stores the monitored voltage across resistor 14 (representing coil current) at regular intervals. The current applied just before the negative voltage spike is measured in connection with diamond 56 for the last actuation and is set as the threshold voltage for the current actuation. Here, at diamond 58, the presently sensed voltage is compared against the previous voltage level that caused armature 24 to actuate. Further alternatively, the voltage stored at block 54 could be incremented slightly to allow for a margin of error. In either case, updating the actuation voltage of a particular solenoid 20 allows system 10 and method 50 to be adaptable for different solenoids within an application or the same solenoid over changing operating conditions. Various operating conditions can affect the operating (and release) levels, including temperature, orientation, external magnetic fields, shock and vibration. Different solenoids based on age and duty cycle will have different actuation voltages. Setting one preset level for all solenoids could, therefore, produce faulty armature-stuck alarms if the level is too low or could force the level to be set so high that power is wasted before determining that the armature is stuck in connection with diamond 58.

In the intended application the solenoid duty cycle (as distinct from PWM duty cycle) can be very high, meaning that solenoid 20 can spend a very long time (e.g., hours) in the hold state relative to the number of actuations and the current rise time of milliseconds, so that the threshold used at diamond 58 has little effect on the overall average power. The hold current is accordingly an important parameter in minimizing overall average power.

When the negative voltage is sensed, as determined in connection with diamond 56, controller 30 in combination with switching device 18 reduces power to solenoid coil 22 to a hold level, as seen in connection with block 62. That is, solenoid 20 requires more power to counter the force of the spring to begin movement than it does to hold the solenoid armature 24 against the spring force once armature 24 is fully actuated. As seen in connection with block 62, control element 30 can be configured to reduce the current once the negative-going spike is sensed. That is, in one embodiment as soon as control element 30 sees the negative-going spike, the control element begins PWM of switching device 18 to reduce the current and power. This reduction in power can occur before armature 24 is fully actuated, reducing the impact force of armature 24 when the armature reaches its end of travel. Such reduction reduces solenoid actuation noise and wear. Alternatively, control element 30 can wait for a short period of time (until the current begins to rise again) before reducing power to ensure that armature 24 has been fully actuated.

Without the feedback voltage to control element 30, the control element has no indication of when armature 24 actuates or if it actuates. Instead, the control element has to assume that solenoid 20 has been fully actuated after providing full power for a period of time before power can be reduced. Using a preset time for full power requires that a safety margin be included in the time that coil 22 is operated at full power, which increases power dissipation and battery drain, assuming that the application operating system 10 has to rely on battery power for normal or power-loss operation. The increased application of full power also increases noise and wear. Furthermore, without the feedback, stuck solenoid detection is not possible.

Once armature 24 is verified to be in the actuated state, the power to coil 22 is reduced to a level required to maintain armature 24 in the actuated state. While in the hold state, as seen at block 64, control element 30 continues to monitor solenoid voltage and current via amplifier 36. At diamond 66 method 50 queries whether it is time to release armature 24. An intentional release of armature 24 occurs if an on/off command from supervisory controller 32 signals an OFF command. If an OFF command is not received, as determined at diamond 66, method 50 also determines if armature 24 has released prematurely, as seen at diamond 68. That is, if supervisory controller 32 still indicates that control element 30 should be maintaining the hold current (e.g., has not yet issued an OFF command), but controller 30 via amplifier 36 sees a (in this case positive-going) current spike, then control element 30 knows that the hold current has been set too low and that armature 24 has been released in error. If no such positive-going current spike is detected (armature 24 is still actuated), as seen in connection with diamond 68, method 50 continues to monitor the voltage in the hold state as seen at block 64, and the above described sub-loop is repeated.

If, however, control element 30 does see a positive-going current spike, as determined in connection with diamond 68 (armature released prematurely), control element 30 increases the previously set hold current (setting of hold current shown below) or sets the hold current to a known safe level, as seen in connection with block 70. An unintentional release can occur as determined at diamond 68, for example, if the solenoid is exposed to vibration or shock after the current is minimized to the hold current. Next, system 10 applies power via PWM and monitors the voltage across resistor 14 as seen at block 54 to immediately re-actuate armature 24, this time reducing the power to coil 22 at block 62 to the level increased at block 70.

When control element 30 receives the OFF signal from supervisory controller 32 indicating that it is time to release armature 24, as determined in connection with diamond 66, control element 30 measures and stores an instantaneous voltage or current level, as seen at block 72. The sensed OFF signal causes control element 30 to then incrementally reduce the duty cycle of the PWM on FET gate 26, which reduces current and thus power at coil 22, as seen in connection with block 74.

In an alternative embodiment, control element can reduce the PWM to zero percent at step 74, which here occurs before step 72. Recirculation diode 34 and the inductance of coil 22 prevent the coil current from dropping instantaneously. Instead, coil current decays over time, allowing control element 30 the opportunity to sense the release. After reducing PWM to zero at step 74, method 50 measures and stores solenoid current at step 72 until positive-going current spike is sensed at diamond 76 or an alert is posted via diamond 78 and block 60 as described herein.

At diamond 76, control element 30 determines if a positive-going current or voltage spike occurs due to the reduced current caused in connection with block 74, which indicates that the armature has been released. If the positive-going current spike is not sensed, as determined in connection with diamond 76, control element 30 determines whether the particular voltage level sensed across resistor 14 should have been low enough for armature 24 to have released (creating positive-going current spike), as determined in connection with diamond 78. That is, based on historical data or a predetermined voltage level, if it is expected that a particular voltage level for solenoid 20 should have released actuator 24, but the positive-going spike has not been detected, then control element 30 in method 50 determines that armature 24 is stuck and posts a solenoid failure-to-release (valve stuck open for one intended application, e.g., tubing not occluded) alarm via acknowledge/error signaling output 38, as seen in connection with block 60. Method 50 then ends as seen at oval 80.

If the positive-going current spike is not sensed, as determined in connection with diamond 76, but the voltage level has not fallen to a level at which armature release is expected, as determined in connection with diamond 78, method 50 returns to step 72 and measures and stores the reduced current level, as seen in connection with block 72. At block 74, control element 30 reduces the current again by an increment and the sub-cycle continues until the positive-going current spike is sensed, as determined in connection with diamond 76.

If the positive-going current spike is sensed, indicating that the solenoid armature 24 has released, as determined in connection with diamond 76, control element 30 at block 79 sets the hold current for block 62 (for the next actuation of solenoid 20) at the most recently recorded current level that has been recorded at block 72. That is, for intentional releases the most previously saved reduced current value is set as the hold current level for the next actuation. Method 50 then ends, as seen in connection with oval 80.

System 10 and method 50 enable each solenoid of an application to have its own hold current threshold. Thus, solenoids that are used more often and wear out more quickly may have higher (or lower) hold currents, while solenoids that are not used as often have lower (or higher) hold currents. This enables each solenoid to be operated at its own unique hold current under a "smart" control either via a separate control element 30 or a master control element 30 controlling multiple solenoids 20.

System 10 can also be configured to detect the presence or absence of tubing for safety mitigation. Prior to the start of therapy, the patient or caregiver has to load tubes or a disposable cassette into operable communication with one or more solenoid pinch valve. To allow for tube loading, solenoid 20 is energized to retract armature 24 (assuming a fail-close solenoid). The force required to retract armature 24 is greatest when the associated tube (or cassette valve port) is not present. The tube pushes against the spring, reducing the resultant force required for retraction of armature 24.

System 10 detects the difference in retraction force by detecting a difference in the current required for retraction. During actuation with no tube present, the point in the current waveform at which the negative-going current spike occurs depends upon the force required for actuation and occurs at a higher level than when the tube is present. The control algorithm of system 10 records the required actuation current prior to tube loading and sets a threshold level at a current less than the recorded current level (but at a level greater than the current required for tube-present actuation).

After tube loading, the pinch valve armature 24 is actuated and released several times during the course of a therapy. If at anytime after tube is loaded (but prior to end of therapy) the retraction current rises above the threshold current, control element 30 generates an alarm output 38, indicating that the tubing is no longer in operable communication with the solenoid valve and allowing the patient or caregiver to take action to prevent potential free flow of dialysate for example.

Figure 3:
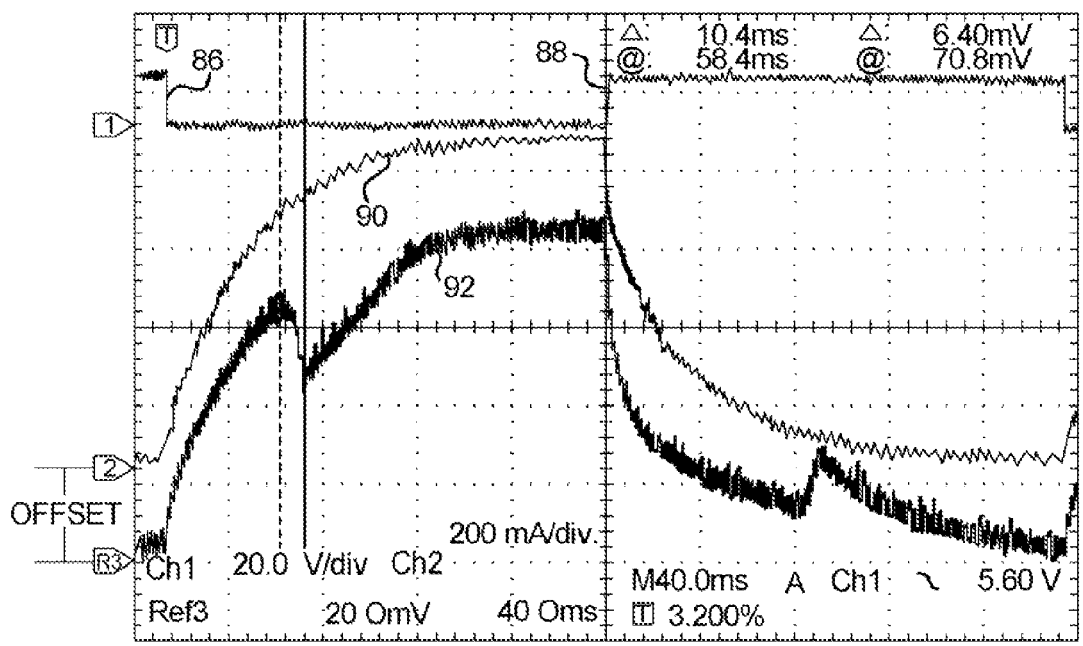
FIGS. 3 to 6 are current versus time plots illustrating various solenoid actuation and release characteristics associated with the system and method of FIGS. 1 and 2.

FIG. 3 illustrates a first plot of current versus time showing the principles of system 10 and method 50. Note that FIGS. 3 to 6 show only waveforms at PWM of 100% (left half of Figures) and 0% (right half of Figures). Here, a first trace (shown at left hand side via flag #1) falling edge 86 highlights where FET 18 is turned on 100% (voltage fully applied to the solenoid coil). A rising edge 88 highlights where the FET 18 is turned off. A second trace 90 (shown at left hand side via flag #2) shows the resultant coil 22 current for a case of a solenoid armature 24 stuck in a non-actuated position. A third trace 92 (shown at left hand side via flag #3) shows the resultant coil current for a case of solenoid armature 24 moving freely with no tube in operable communication with the solenoid valve. Second and third traces 90 and 92 are offset in FIG. 3 for clarity.

Figure 4:
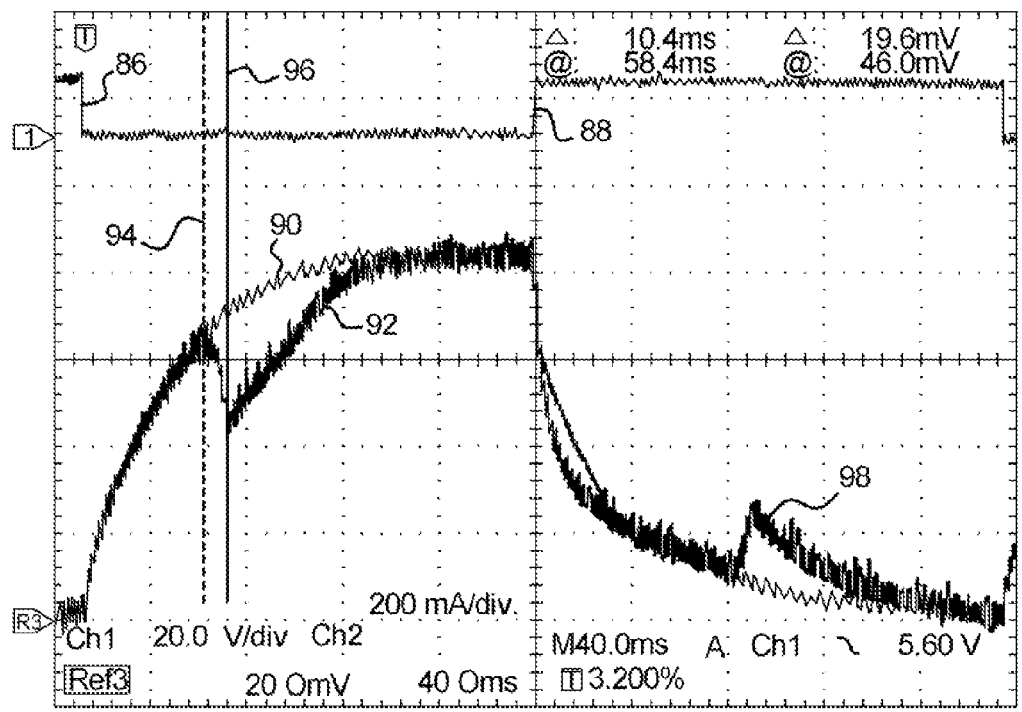

FIG. 4 illustrates a second plot of current versus time showing the same plot as FIG. 3, except that the offset between the second and third current traces 90 and 92 is removed, showing the difference in wave shapes. Note that second trace 92 clearly shows (in the left half of the screen) the negative spike that occurs due to the movement of the armature 24 relative to the coil 22 of solenoid 20. Vertical cursors 94 and 96 approximate the beginning time and end time respectively of the movement of armature 24. The right half of the plot of FIG. 4 shows the positive spike 98 that occurs in waveform 92 when armature 24 of solenoid 20 releases.

Figure 5:
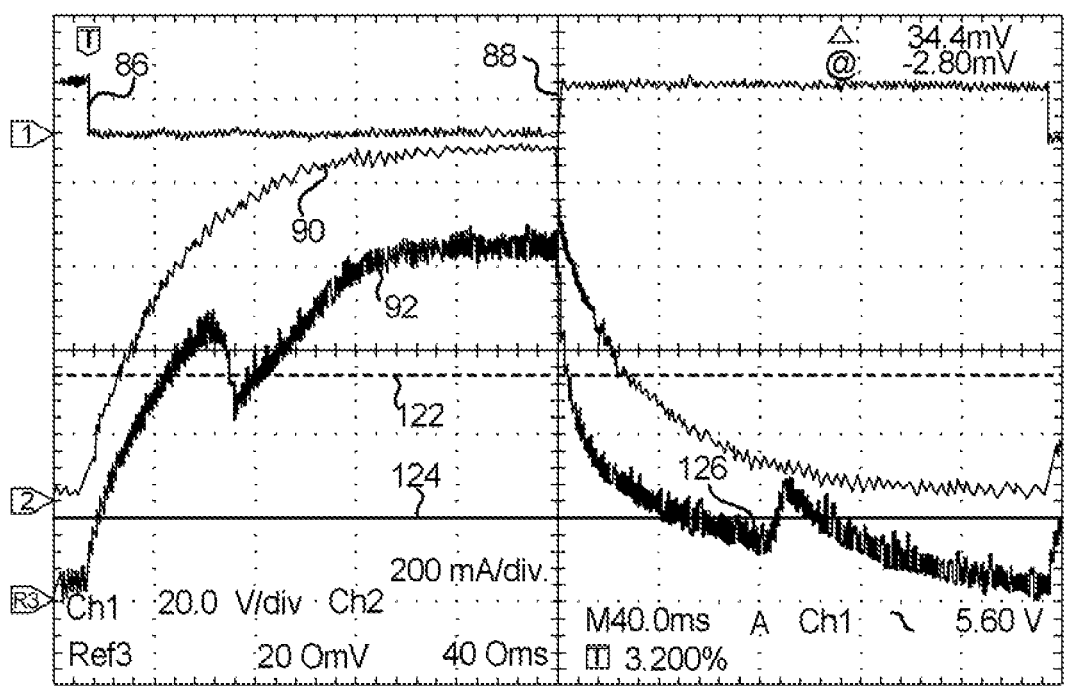

FIG. 5 shows the same plot as FIG. 3, except that horizontal cursors 122 and 124 are shown. Top (dashed) cursor 122 shows an approximate point in the falling portion of the negative spike of second current waveform 92 at which control element 30 could begin to apply PWM to reduce the current to solenoid coil 22. Lower (solid) cursor 124 shows the approximate point where PWM could set the current that is slightly greater than the release point 126. Release point 126 is visible in the right half of the second trace 92 at the point that current suddenly begins to rise (approximately 2 cm right of center, e.g., at about 80 milliseconds).

Figure 6:
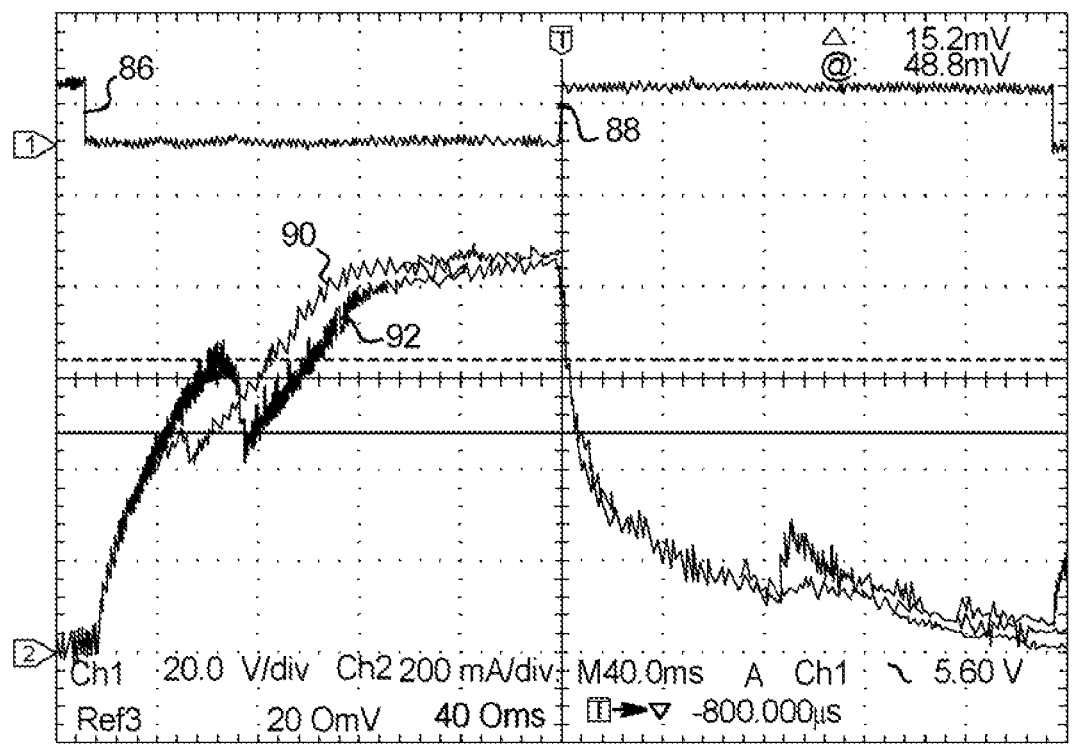

FIG. 6 shows second waveform 90 for the case in which a tube is loaded in position with solenoid 20. The horizontal cursors 122 and 124 are placed at the point in each current waveform 90 and 92 at which armature 24 begins actuation. Each vertical division is 200 mA. For unloaded trace 92, armature movement starts around 640 mA (dashed cursor 122 at 0.2 cm above center). For tube-loaded trace 90, armature 24 starts to move at cursor 124 at about 480 mA (solid cursor 0.6 cm below center). If a threshold level is set at, for example, 560 mA (0.2 cm below center), control element 30 would interpret first trace 90 correctly as "tube present" and interpret second trace 92 correctly as "tube not loaded". Note that the time of the start of movement (start of negative spike) is less for the second trace 90 (for tube present) than for third trace 92 (for no tube present) so that a time difference measurement between start of 100% duty cycle (point 86 one first waveform) and the minima of the negative spike could also distinguish or further confirm tube loaded versus non-loaded conditions. An accurate time measurement can be made from the falling edge 86 of first waveform to the minima of negative current spike (e.g., ~40 milliseconds for tube present and ~60 milliseconds for no tube present).

Solenoid Control System Having Temperature Compensation

Figure 7:
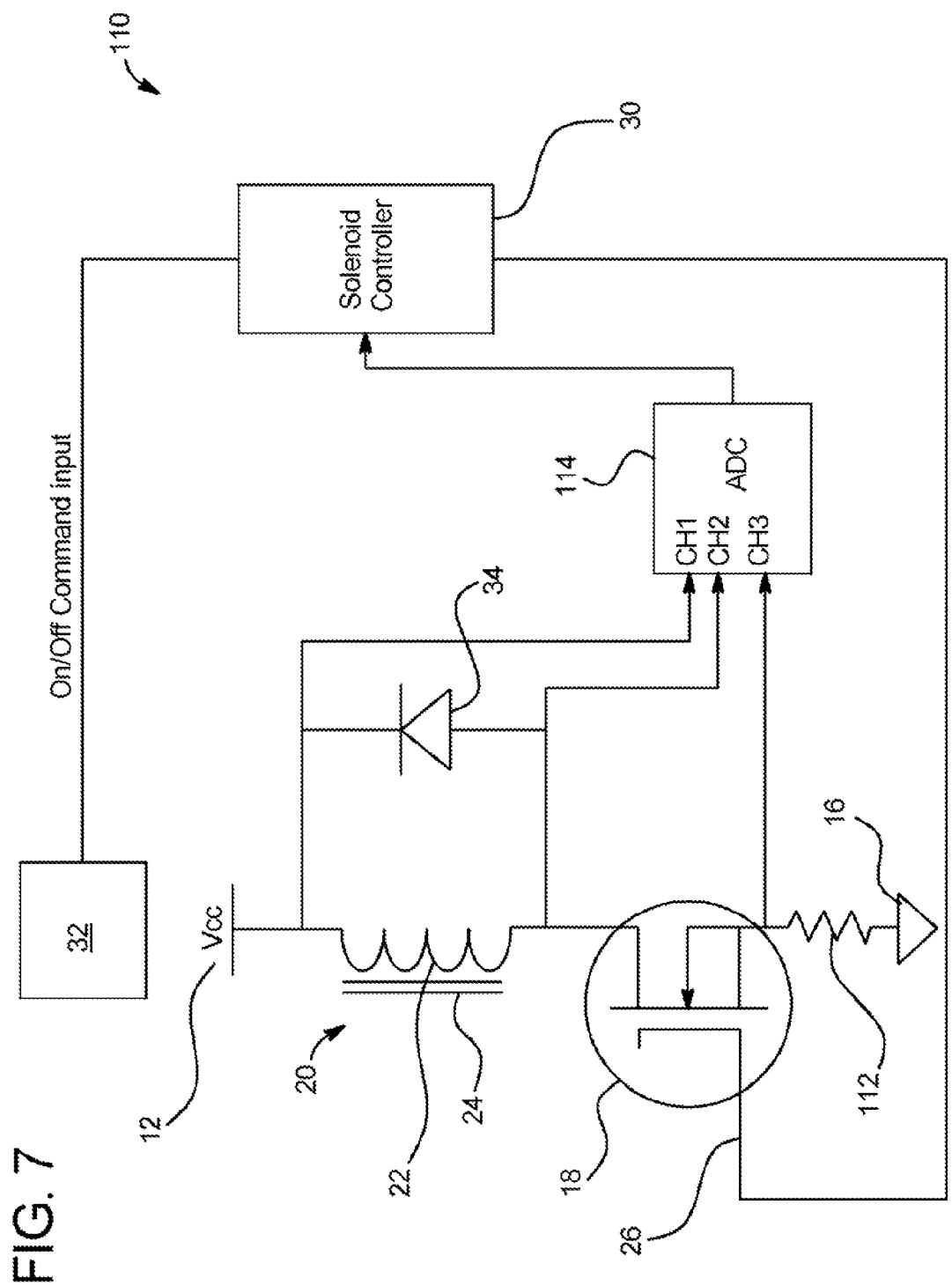
FIG. 7 is a schematic diagram illustrating another embodiment of a solenoid actuation system of the present disclosure.

Referring now to FIG. 7, system 110 illustrates an alternative solenoid control system. As before, solenoid 20 can be used in a medical fluid application, such as one in which a tube is occluded or not occluded to allow a medical fluid to be delivered to a patient. In one particularly well suited embodiment, system 110 is employed in a dialysis application, such as peritoneal dialysis or hemodialysis.

System 110 includes many of the same components as system 10. Those components are numbered the same in system 110. In particular, system 110 includes a supervisory controller 32, which commands a local solenoid control element 30. Solenoid control element 30 can control a single solenoid 20 or multiple solenoids as discussed with system 10. As before, control element 30 controls current flow from source 12 through coil 22 of solenoid 20 via a switching device 18, such as a FET. Control element 30 uses PWM at gate 26 of FET 18 to control current flow from power source 12, through solenoid coil 22, to ground 16, which provides a current return path to power supply 12.

Power source 12 in one embodiment is a direct current ("DC") power supply. Control element 30 includes processing and memory as discussed above. When switching element 18 is switched off, a recirculation current continues to flow for a short period of time through solenoid coil 22 of solenoid 20 via diode 34. When switching element 18 is switched on, however, no current flows through diode 34. Accordingly, during periods when switching element 18 is switched on, all current that passes through coil 22 also passes through a resistor 112, which is located between switching element 18 and ground 16.

System 110 also includes an analog to digital converter ("ADC") 114. ADC 114 as illustrated includes three channels CH1, CH2 and CH3. ADC 114 in an embodiment also includes an amplifier, such as amplifier 36 shown in system 10. Alternatively, an amplifier is provided externally to ADC 114.

Again, to maintain I2R power losses at a low level across resistor 112, the resistance of resistor 112 in one embodiment is made low, e.g., on the order of milliohms. This results in a low voltage drop across resistor 112. That low voltage is amplified at or before ADC 114 (not illustrated but could use amplifier 36 shown in system 10). ADC 114 can include on-board signal amplification at one or more of its channels.

Resistor 112 in system 110 is connected to ground 16 as shown. Accordingly, the voltage measured at CH3 across resistor 112 is ground referenced, allowing a single ended input at ADC 114 to be used. In an alternative configuration, resistor 112 can be located in series with solenoid coil 22, like in system 10, which requires a differential input at ADC. Although not shown in FIG. 7, analog filtering can be incorporated on all ADC inputs CH1, CH2 and CH3. In one embodiment, a RC filter is used at each input CH1 to CH3.

Figure 8:
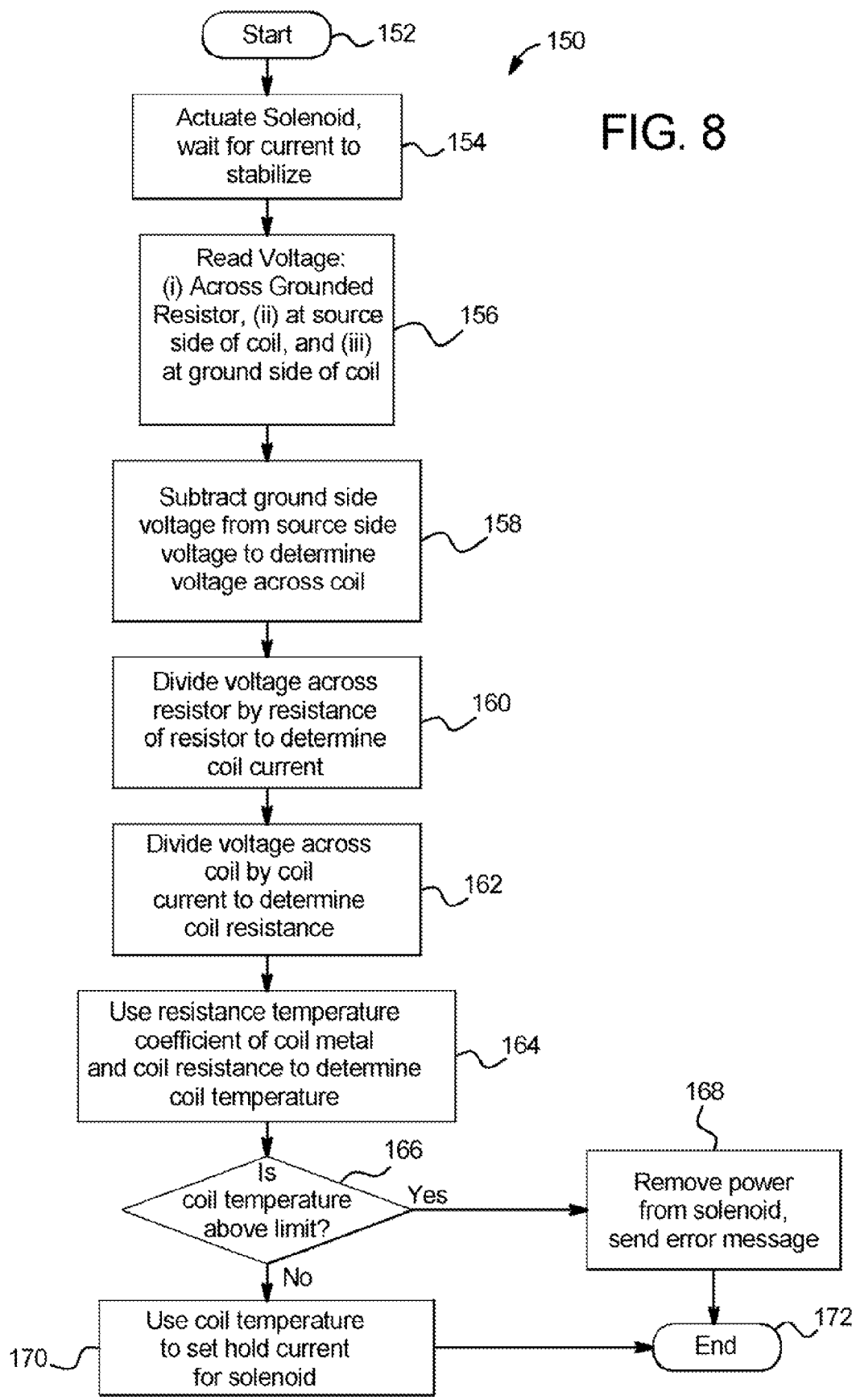
FIG. 8 is a logic flow diagram illustrating one embodiment of a method of operating the system of FIG. 7.

Referring additionally to FIG. 8, one method 150 for operating the circuitry of system 110 is illustrated. Upon beginning method 150 at oval 152, control element 30, upon receiving a solenoid activation signal from supervisory controller 32, supplies voltage to FET gate 26 which switches on FET 18 and enables current to flow from power source 12 to ground 16, through coil 22. Full voltage is provided across coil 22, causing current to rise and causing armature 24 to begin to actuate, as seen in block 154. Also in block 154, method 150 waits for a predetermined time to allow armature 24 to fully actuate and for the current to stabilize (e.g., one hundred milliseconds). At block 156, control element 30 via ADC 114 reads the voltage across resistor 112, which is proportional to current flowing through coil 22. The voltage across resistor 112 is converted at CH3 of ADC 114, which is then sent to control element 30. Control element 30 also reads (i) a voltage at the junction of source 12 and coil 22 at CH1 and (ii) the voltage at the junction of coil 22 and switching device 18 at CH2. Thus at block 156, control element 30 reads three different voltages.

At block 158, control element 30 subtracts the CH2 voltage signal at the switching device side of coil 22 from the CH1 voltage signal at the supply side of coil 22 to determine a voltage drop across coil 22. At block 160, control element 30 divides the voltage sensed at CH3, which is the voltage across resistor 112 to ground, by a known resistance of resistor 112 to determine the amount of current flowing from source 12 to ground 16. As discussed above, since no current flows through diode 34 when switching device 18 is switched on, the current determined in connection with block 160 is the total current flowing through coil 22. It should be appreciated that the procedures of blocks 158 and 160 can be performed at the same time or either one in advance of the other but close enough in time (milliseconds) so that temperature of solenoid coil 22 does not change significantly during the time between each of the three readings.

At block 162, control element 30 divides the voltage determined across coil at block 158 by the coil current determined at block 160 to further determine a resistance of coil 22. As seen at block 164, the resistance of solenoid coil 22 changes as a function of temperature in a predictable way. Indeed the material of coil 22 has a temperature coefficient of resistance, which relates a change in resistance to a change in degree Celsius or degree Fahrenheit. For example, copper has a resistance temperature coefficient of 0.393% change in resistance for every change in degree Celsius. Therefore, control element 30 can, at block 164, determine coil temperature by determining the resistance at block 162 knowing one resistance data point at a particular degree Celsius (e.g., knowing the resistance of coil 22 at 25° C.) and knowing the temperature coefficient of resistance of the metal (e.g., 0.393% per degree Celsius) using the following formula: $t2=((Rt2-Rt1)/(Rt1*\alpha))+t1$, where $t2$ is the resultant temperature, $Rt2$ is the coil resistance determined a block 162, $Rt1$ is the reference coil resistance at a known temperature $t1$, and $\alpha$ is the temperature coefficient of resistance of the metal. The values of $\alpha$, $t1$ and $Rt1$ are previously provided to control element 30 during a calibration phase. Alternatively, control element 30 or supervisory controller 32 stores a table relating different increments of resistance to different temperatures for the particular metal of coil 22. In any case, at block 164, method 150 determines a coil temperature from the determined coil resistance.

At diamond 166, if the temperature determined is above a temperature limit, control element 30 removes voltage from gate 26 of switching device 18, such that the switch opens and power is removed from coil 22, as seen at block 168. Also, control element 30 and supervisory controller 32 can be configured to cause the application in which the system 110 is provided to send an alert or an alarm to the patient, nurse or other caregiver. If the coil temperature is below a temperature limit, method 150 uses the temperature to determine and set a hold current for solenoid coil 22 as discussed in detail below. Method 150 then ends as seen at oval 172.

As discussed herein, when armature 24 is fully actuated, control element 30 can decrease the current to coil 22 to a lower level (hold current) than the level needed to actuate armature 24. It is known that the hold current for a solenoid is effected by various factors such as coil temperature, vibration, solenoid aging and manufacturing unit to unit variations. If those factors were not present, the hold current could be made less because a safety margin would not be needed. But since the factors are present, control element 30 must set the hold current to a greater value to ensure that coil 22 holds armatures 24 in the actuated position under a worst case combination of the above factors. In the present system and method, however, knowing the coil temperature enables system 110 to compensate for the effects of temperature, effectively removing temperature as a factor. Indeed, it has been found with solenoid system 110 applied in a medical fluid occlusion application, temperature compensation allows the hold power to be reduced by a factor of about 44 percent. This is a significant power savings which is important in a solenoid system that may operate on a battery backup.

Reduced hold power is achieved using PWM via control element 30 and switching element 18. Switching the element 18 on and off at a repeated rate (e.g., on the order of kHz) using PWM causes current through solenoid 20 to be maintained at a level proportional to the duty cycle of PWM voltage waveform applied to FET gate 26. When switching element 18 is switched on, control element 30 creates a voltage across resistor 112 that is proportional to coil 22 of solenoid 20 as discussed above. For increasing coil temperatures, the hold current is increased to compensate for increased losses in solenoid holding ability due to the increased temperature. At lower coil temperatures, hold current can be reduced thus achieving a power savings. Power reduction achieved at lower coil temperatures helps to reduce the self-heating of coil 22 and maintains an average coil operating temperature at a lower level than would result if temperature compensation for the hold current is not used. Lower average operating temperature in turn translates into an improved reliability for both solenoid 20 and any adjacent circuit components.

In one embodiment, a table is formed relating coil temperature to hold current. The table can be formed empirically. Thus, when a coil temperature is determined that is below the limit as seen at diamond 166 of method 150, control element 30 finds a hold current corresponding to the determined temperature from the table and sets the hold current accordingly using PWM at block 170.

Although not shown in FIG. 8, it is contemplated to repeat the steps of method 150 periodically during the hold state operation of solenoid 20 beginning at step 156. During the hold state, armature 24 is not re-actuated at step 154. However, the coil voltage and coil current can be determined in the same manner at steps 158 and 160 during the part of the PWM waveform when FET 18 is switched on, causing the current flowing in coil 22 to flow through resistor 112. Coil resistance is re-determined and the hold current is updated using the above described table. In this manner, coil current can be updated repeatedly during the hold state of solenoid 20. If the temperature of coil 22 rises, hold current rises as described above. If the temperature of coil 22 falls during hold, the hold current can be lessened even further. Alternatively, the hold current is held constant during the hold state of solenoid 20.

Referring now to FIG. 9, a table containing empirical data relating coil temperature to hold current is illustrated. The table shows that that the holding current threshold shown at column 126 increases with coil temperature shown at column 132, indicating a decrease in solenoid efficiency with an increase in temperature. Column 128 shows a resulting holding power threshold in watts. If it is assumed that a maximum ambient temperature of 70° C. exists, that the solenoid coil to ambient thermal resistance is 10° C./watt (previous determined during testing) and that a holding power of 1 watt exists, then the coil temperature could reach 80° C. As seen in column 128, 80° C. in column 132 results in a holding power threshold of about 0.74 watts, which is about a 50% (0.74–0.49/0.49) increase over the holding power threshold at 22.3° C. In other words, at least about 50% of the power that the pinch valves require can be saved if the holding current is adjusted according to coil temperature (and if the coil temperature is at the lower temperature of 22.3° C.).

System 110 monitors coil current and coil voltage and controls coil current via PWM, as discussed herein, to determine and set a minimum hold current to achieve minimum hold power. System 110 can also monitor the coil current via ADC 114 to look for a current transient that would occur if solenoid 20 releases due to the hold current setting being too low (assuming the ADC is fast enough). Here, system 110 is configured to apply full PWM power quickly to reactuate the solenoid 20, after which system 110 increases to a slightly greater holding current to reduce the likelihood of repeated unintended release.

It should be appreciated that a combination of system 10 and 110 can be formed to provide a solenoid circuit having the advantages of both systems 10 and 110. ADC 114 in system 110 can be a lower speed ADC than the one implemented with control element 30 of system 10. Thus, if for cost savings a slower ADC is chosen, the benefits of system 110 may only be available. The relatively high speed ADC needed for system 10 provides the added capability of verification of solenoid operation. It is therefore contemplated to add the Vcc measurement capability of system 110 to system 10, such that system 10 could then have the benefits of both systems described above. The addition of the Vcc measurement to system 10 could be done for relatively little cost, e.g., if the Vcc measurement is made with a spare ADC channel.

Multiple Line Voltage Fluid Heater

Figure 10:
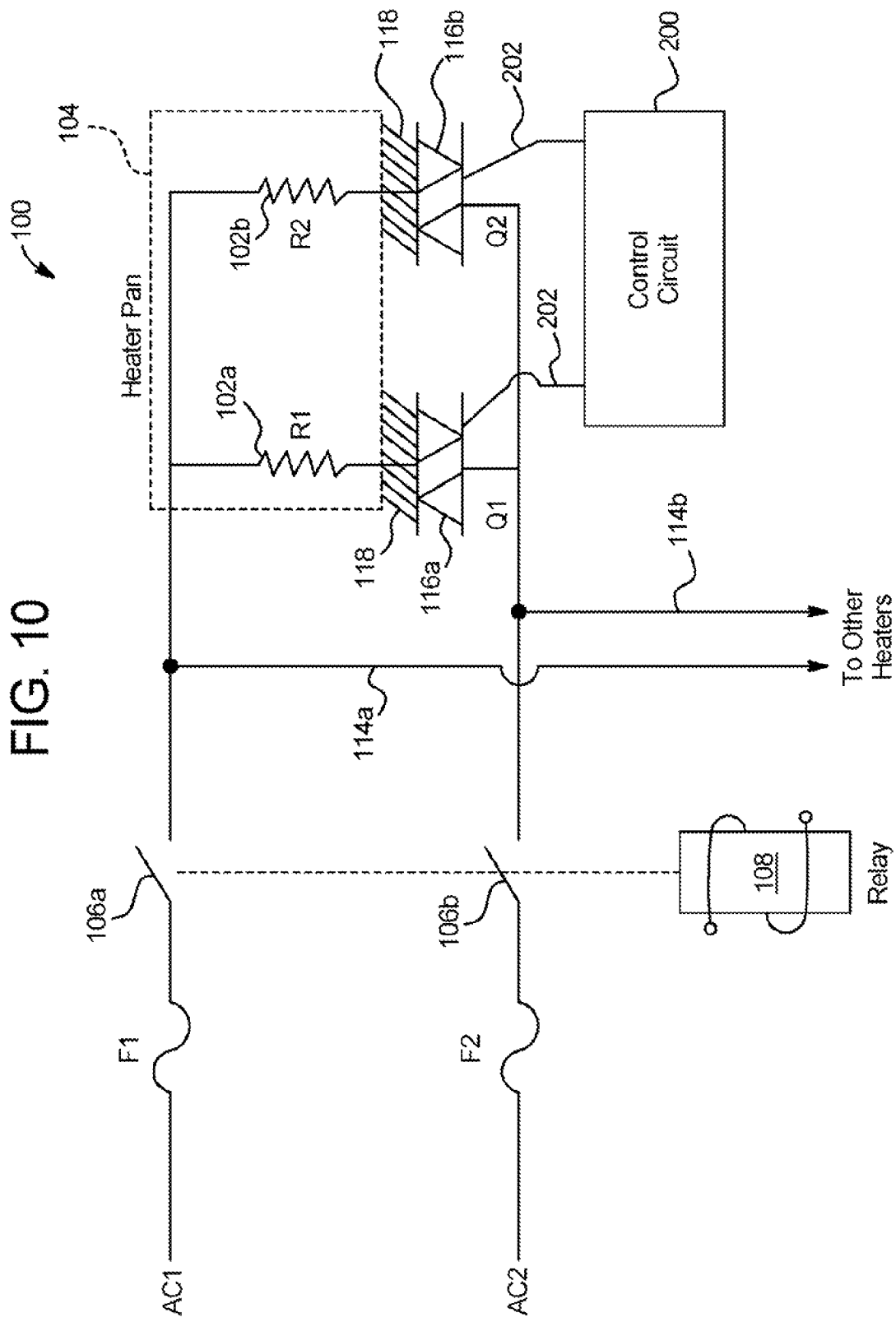
FIG. 10 is a schematic diagram of one embodiment of a multiple line voltage heating system of the present disclosure.
Figure 11:
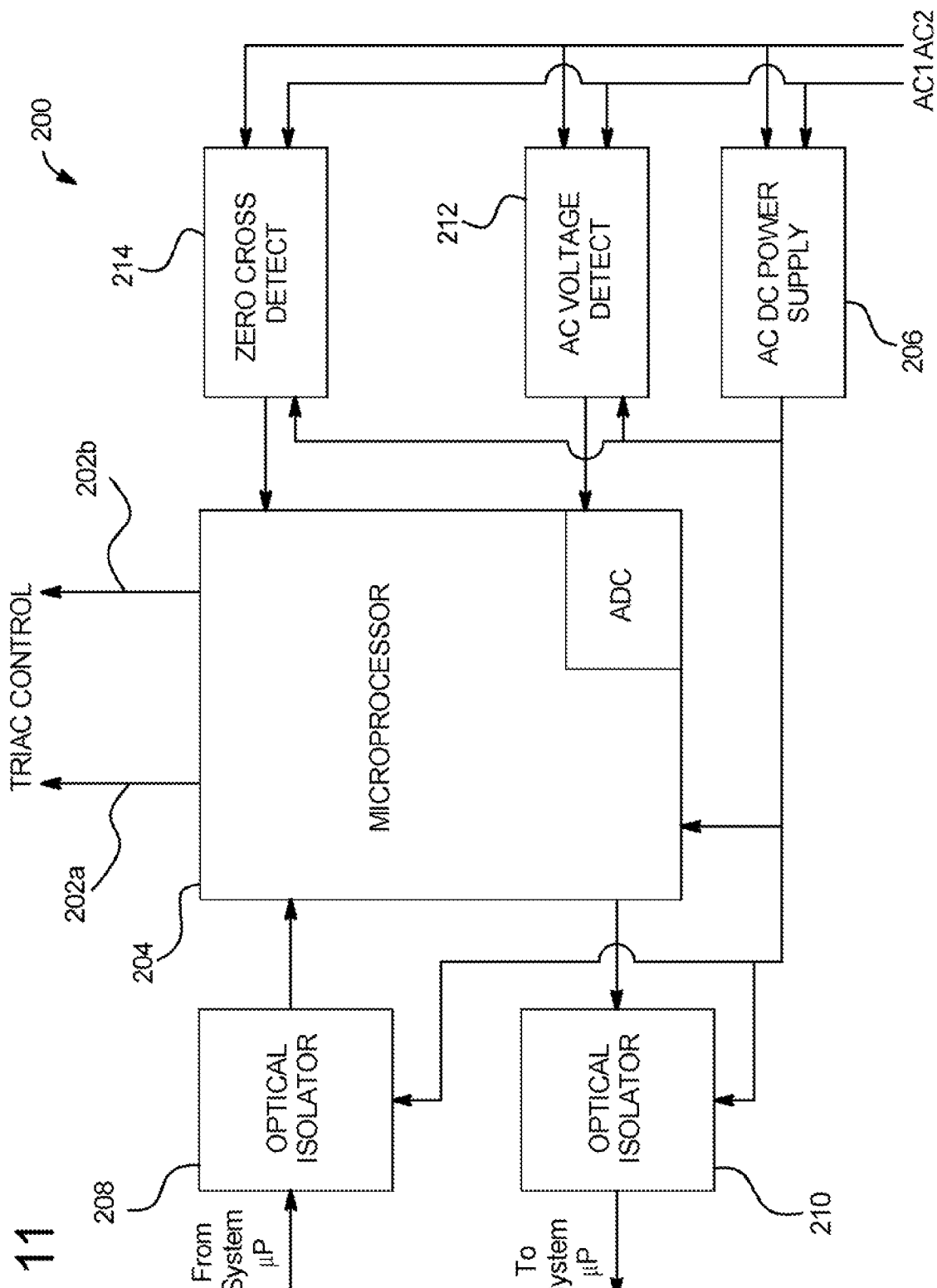
FIG. 11 is a schematic diagram of one embodiment of a control architecture for the heating system of the present disclosure in which dual heater resistances are varied.

Referring now to FIGS. 10 and 11, system 100 including control circuit 200 illustrates one embodiment for a fluid heating system operable with different supply line voltages. Either solenoid system 10 or 110 or a hybrid of systems 10 and 110 can operate in a fluid delivery system with heating circuit 100 shown in FIG. 10. Control circuit 200 controls heating circuit 100 as described in detail below in connection with FIG. 11. Circuit 100 includes a pair of bifilar, serpentine or spiral wound heater elements 102a and 102b having resistances R1 and R2, respectively. The values of resistance for R1 and R2 are discussed below and are different in the illustrated embodiment.

Heater pan is shown at phantom line 104 to indicate that resistive heating elements 102a and 102b are located at or on heater pan 104. AC1 is a connection at one side of an AC power line to elements 102a and 102b. AC2 is the connection at the other side of the AC power line to the heating elements. AC line power can, for example, have any AC line voltage from about 94 VAC to about 264 VAC and operate at a frequency range of about 47 to about 63 Hz line frequency.

System 100 is able to detect the AC line voltage automatically and configure itself accordingly. System 100 uses two resistive heating elements 102a and 102b of different resistances thus minimizing the number of switching components, lowering cost and lessening known failure modes. As illustrated, power lines AC1 and AC2 are fused at fuse F1 and F2, respectively. Alternatively, a single fuse protects AC1 and AC2. Power lines AC1 and AC2 are also connected respectively to switches 106a and 106b which, in one embodiment, are switches of a mechanical coil relay 108 or are a plurality of such relays. Switches 106a and 106b serve to cutout power to the entire heating circuit 100 if necessary. Relay 108 is controlled for example by a supervisory controller of the application, e.g., a supervisory controller or central processing unit ("CPU") of a dialysis machine. A soft key, hard key or touch screen input from the control panel of the dialysis instrument in one embodiment initiates the cut-out sequence. Alternatively or additionally, the cut-out sequence is initiated automatically. In an alternative embodiment, one or more solid state switch, manual switch or TRIAC (described below) replaces coil relay 108 and switches 106a and 106b. Circuit 100 can control multiple heating pans 104 and heating elements 102a and 102b. Power lines 114a and 114b tap power off lines AC1 and AC2, respectively, to provide power to their additional heaters. As illustrated, switches 106a and 106b are configured to cut power to each of the heaters powered by lines AC1 and AC2. Alternatively, additional fusing can be applied past the point of where power lines 114a and 114b tap power off lines AC1 and AC2 so that separate fusing is applied to each of the heaters.

For each heater or heater pan and associated heater element powered via AC1 and AC2, switching elements 116a and 116b are provided (one switching element per each heater element). Switching device 116a controls heater element 102a while switching device 116b controls heater element 102b. For the equations discussed below, symbol Q1 represents switching element 116a while symbol Q2 represents switching element 116b. Further, character R1 represents the resistive value of heating element 102a while character R2 represents the resistive value of heating element 102b.

In one embodiment, switching elements 116a and 116b are triodes for alternating current ("TRIACs"), which are approximately equivalent to two silicon-controlled rectifiers (SCRs/thyrisors) joined in inverse parallel (parallel but with the polarity reversed) and with their gates connected together. TRIACs 116a and 116b are bidirectional electronic switches that can conduct current in either direction when triggered (energized). TRIACs 116a and 116b can be triggered by either a positive or a negative voltage being applied to their gate electrodes. Once triggered, the TRIACs continue to conduct current until the current flow drops below a certain threshold value, such as at the end of a half-cycle of alternating current ("AC") mains power. TRIACs are therefore convenient for AC circuits, allowing for the control of large power flows to heating elements 102a and 102b with milliampere-scale control currents from control element 200. Control element 200 can be configured to apply a trigger pulse to the TRIAC gates at a particular point in an AC cycle, allowing control over the percentage of current that flows through the TRIAC to heater elements 102a and 102b. However, for this invention, the trigger is only applied near the zero crossing point of the AC waveform in order to minimize the conducted EMI emissions generated by the switching. This means that the heater is fully activated for the duration of each half cycle in which it is triggered. To control heating, the heater elements are pulse width modulated at a low frequency relative to the 50 or 60 Hz cycle rate of the AC power so that the heaters are on for multiple AC cycles and then off for multiple AC cycles.

In an alternative embodiment, switching devices 116a and 116b include two silicon controlled rectifiers ("SCRs") positioned in inverse parallel with respect to each other. Here, each SCR has an entire half-cycle of reverse polarity voltage applied to it, which assures turn-off of the SCRs regardless of the character of the load heating elements 102a and 102b. Such configuration provides an advantage if loads 102a and 102b are inductive rather than resistive (resistive embodiment shown in circuit 100). TRIACs can sometimes have self-triggering problems when switching inductive loads, making the use of SCRs with inductive loads more attractive.

Switching elements 116a and 116b in one embodiment are heat sinked to, but electrically isolated from, heater pan 104 via double electrical insulation 118. Electrical insulation 118 can for example be layers of Kapton® tape or sheet compressed between switching elements 116 (referring collectively to elements 116a and 116b) and a metal surface or heat sink of heater pan 104. The, e.g., Kapton® tape, insulation 118 is thermally conductive but electrically insulating. Such heat sinking allows the several watts of heat that TRIACs 116 generate and transfer to pan 104 to be used to further heat medical fluid in thermal communication with the pan (in one intended application the dialysate is contained in plastic bags that rest on a heater pan, such that the liquid has no direct contact with the heater pan). Such heat sinking increases heating efficiency and reduces cost by eliminating an additional heat sink, which might otherwise be necessary.

Q1 and Q2 as discussed above are TRIAC in an embodiment that switches AC power to elements 102a and 102b, respectively. When AC voltage is 120 VAC (nominal), control circuit 200 (discussed in detail below) causes both switching element 116a and 116b to be on, such that power flows through both heating elements 102a and 102b in parallel. When AC voltage is 240 VAC (nominal), control circuit 200 switches only switching device 116a on so that only element 102a is activated. The variation of power to the heater elements in combination with the varied resistances of elements 102a and 102b shown below results in a consistent power output regardless of the AC line voltage.

In system 100, the resistance R1 of element 102a and the resistance R2 of element 102b are different so that the same power output is provided from heater pan 104 to the liquid being heated regardless of line voltage. Where the nominal high voltage AC (240 VAC) is two times the nominal low voltage AC (120 VAC), the required ratio of resistances between heating elements 102a and 102b is for R1 of 102a to be three times the resistance R2 of element 102b. Such finding is derived as follows, where it is assumed that V1 equals 120 Vrms, V2 equals 240 Vrms, Rp is the resistance of the parallel combination of R1 and R2 and P is a desired heater power, which is again is the same for both voltages V1 and V2:

For 120 VAC operation, (1) $P = V1^2/Rp$
For 240 VAC operation, (2) $P = V2^2/R1$
P as desired is the maximum heater power and is the same for both 120 and 240 VAC operation, so $$V1^2/Rp = V2^2/R1, \text{ also (4) } V2 = 2V1 \qquad (3)$$

Substituting (4) into (3) yields (5) $V1^2/Rp = (2V1)^2/R1$, which can be rearranged as:

$$(2V1)^2/V1^2 = R1/Rp \text{ or} \qquad (6)$$

$$R1/Rp = 4V1^2/V1^2, \text{ canceling } V1^2 \text{ to get} \qquad (7)$$

$$R1/Rp = 4 \qquad (8)$$

(9) Equation for two resistances in parallel is $1/Rp = 1/R1 + 1/R2$

Substituting (9) into (8) yields (10) $R1 (1/R1 + 1/R2) = 4$ or $$1 + R1/R2 = 4, \text{ yielding} \qquad (11)$$

$$R1/R2=3, \text{ or} \qquad (12)$$

$$R2=R1/3 \qquad (13)$$

R1 is determined having the desired maximum power and using equation (2). R2 is then determined from known R1 and equation (13).

Referring to FIG. 11, a block diagram of control circuit 200 illustrates one circuit for controlling dual line voltage heating system 100 of FIG. 10. With control circuit 200 of FIG. 11, each of TRIACs 116a and 116b receives control signals 202 from a micropower 204. Control Signals 202a and 202b correspond to the signals from control circuit 200 (shown as a block in FIG. 10) to system 100 in FIG. 10. Microprocessor 204 is powered via a relatively low power AC-to-DC power supply 206 whenever line voltage is present on AC1 and AC2. Power supply 206 in the illustrated embodiment also supplies DC power to optical isolators 208 and 210 (or isolation transformers), AC voltage detect circuit 212 and zero cross detect circuit 214 whenever line voltage on AC1 and AC2 is present. AC power lines AC1 and AC2 supply power to power supply 206 downstream from switches 106a and 106b of FIG. 5, such that the switches can cut power to supply 206 in one embodiment. Zero cross detect circuit 212 eliminates electromagnetic interference ("EMI") that TRIACs 116a and 116b would generate if microprocessor 204 switches the TRIACs on when the AC voltage waveform is not near zero.

When microprocessor 204 receives a command from a higher-level system processor (via optical isolator 208 or alternatively an isolation transformer) to activate the heater element 102a and/or 102b, microprocessor 204 reads the AC voltage from AC voltage detect circuit 212 via an analog-to-digital converter ("ADC") located onboard microprocessor 204 in the illustrated embodiment. If the reading from AC voltage detect circuit 212 indicates that the AC voltage is 120 Volts (or close to 120 VAC), microprocessor 204 is configured to drive TRIAC signals 202a and 202b to both TRIACs 116a and 116b. If, however, the reading from the AC voltage detect circuit 212 indicates that the AC voltage is 240 Volts (or close to 240 VAC), microprocessor 204 is configured to drive only signal 202a to TRIAC 116a.

Microprocessor 204 then waits for an indication from zero cross detect circuit 214 that the AC voltage is near the zero voltage crossing. Upon receiving the zero cross indication from zero cross detect circuit 214, microprocessor 204 immediately drives signal 202a to TRIAC 116a only (for 240 VAC) or signals 202a and 202b to TRIACs 116a and 116b, respectively, if the AC voltage reading indicates 120 volts. Microprocessor 204 then sends an acknowledgment to the higher-level system processor via optical isolator 210 (or isolation transformer) that the heater element 102a (or elements 102a and 102b) has been activated. Microprocessor 204 triggers the appropriate TRIAC(s) on the zero cross of every half AC half cycle to maintain TRIAC conduction until the microprocessor receives a command from the higher-level system processor via optical isolator 208 (or isolation transformer) to turn the heater off (on or both elements off). Microprocessor 204 then deactivates the TRIAC signal 202a, or signals 202a and 202b, and sends an acknowledgment to the higher-level system processor via optical isolator 210 (or isolation transformer) that the heater has been turned off.

Figure 12:
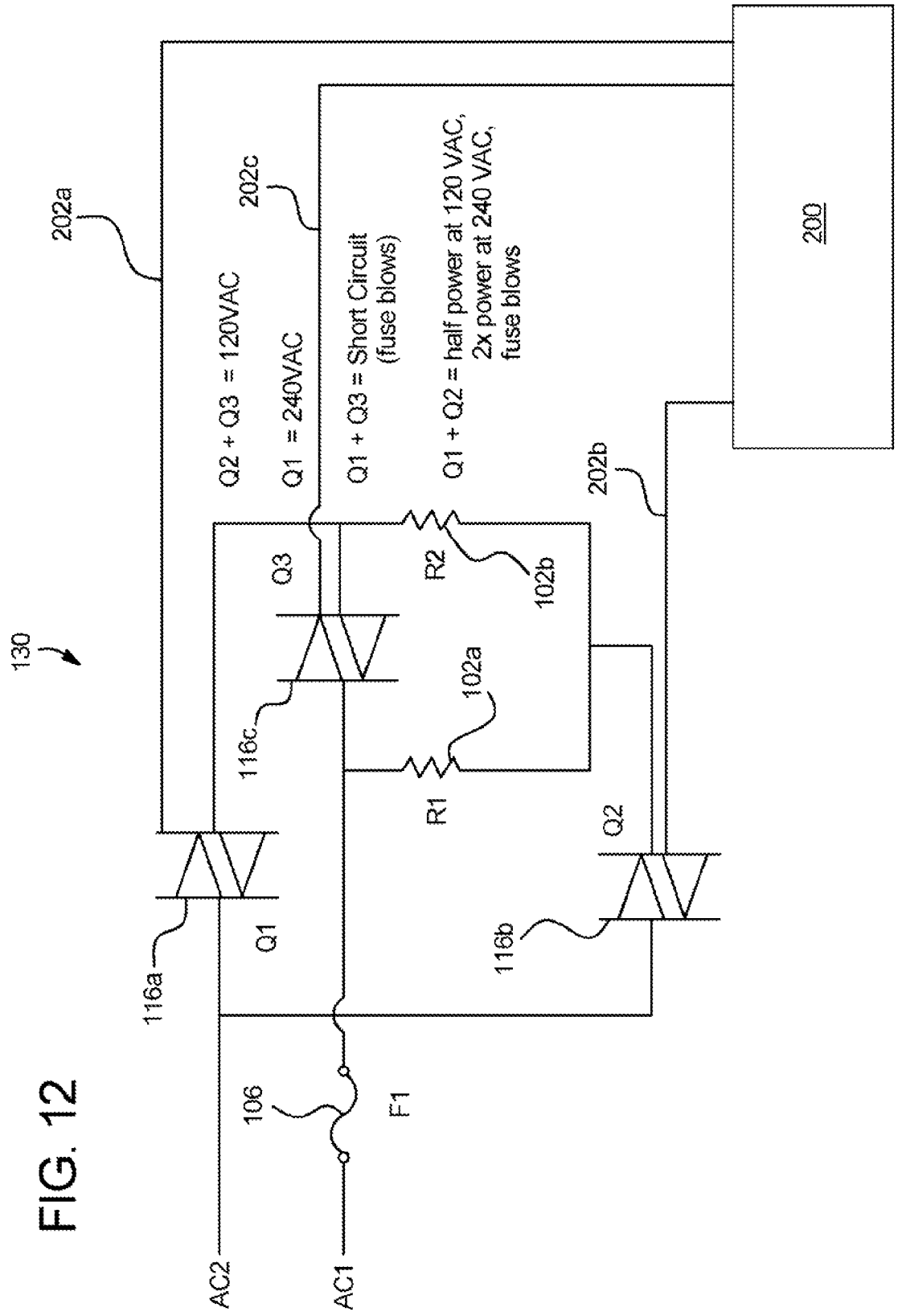
FIGS. 12 and 13 are schematic diagrams of embodiments for a multiple line voltage heating system of the present disclosure in which dual heater resistances are equal.

Referring now to FIG. 12, system 130 illustrates an alternative resistive heating system, in which resistances $R_1$, and $R_2$ of elements 102a and 102b, respectively, are equal. Using elements 102a and 102b of equal resistance is advantageous because it simplifies the manufacturing of the heater as two identical elements are used. Here, however, three switching elements (referred to collectively as 116) are needed instead of two for system 100. Also, circuit 200 requires additional logic or electronics to prevent errant microprocessor behavior from inadvertently driving TRIAC Q1 and TRIAC Q2 simultaneously which can short circuit power lines AC1 or AC2. System 130 accordingly includes lines AC1 and AC2 and three TRIACs or switching devices 116a to 116c. In system 130, if 240 VAC operation is sensed (voltage across AC1 and AC2 is at or near 240 VAC) only switch Q1 116a is actuated, providing an electrical series connection of heating elements 102a and 102b. If 120 VAC operation is sensed (voltage across AC1 and AC2 is at or near 120 VAC), TRIAC Q2 116b and TRIAC Q3 116c are both activated, placing heater elements 102a and 102b in parallel. Control circuit 200 for controlling system 130 includes microprocessor 204, power supply 206, isolators 208 and 210, AC voltage detect circuit 212, zero cross detect circuit 214, as described above, and three TRIAC signal lines 202a, 202b and 202c (as seen in FIG. 12). The operation of control circuit 200 for system 130 is similar to that for system 110, with the main difference being the different switch state control for 120 VAC versus 240 VAC operation.

Note that if both TRIACs Q1 and Q3 (116a and 116c) are activated inadvertently, the AC lines are shorted causing fuse 106 to open. The additional control circuitry described below in connection with FIG. 13 attempts to prevent such shorting from occurring.

Figure 13:
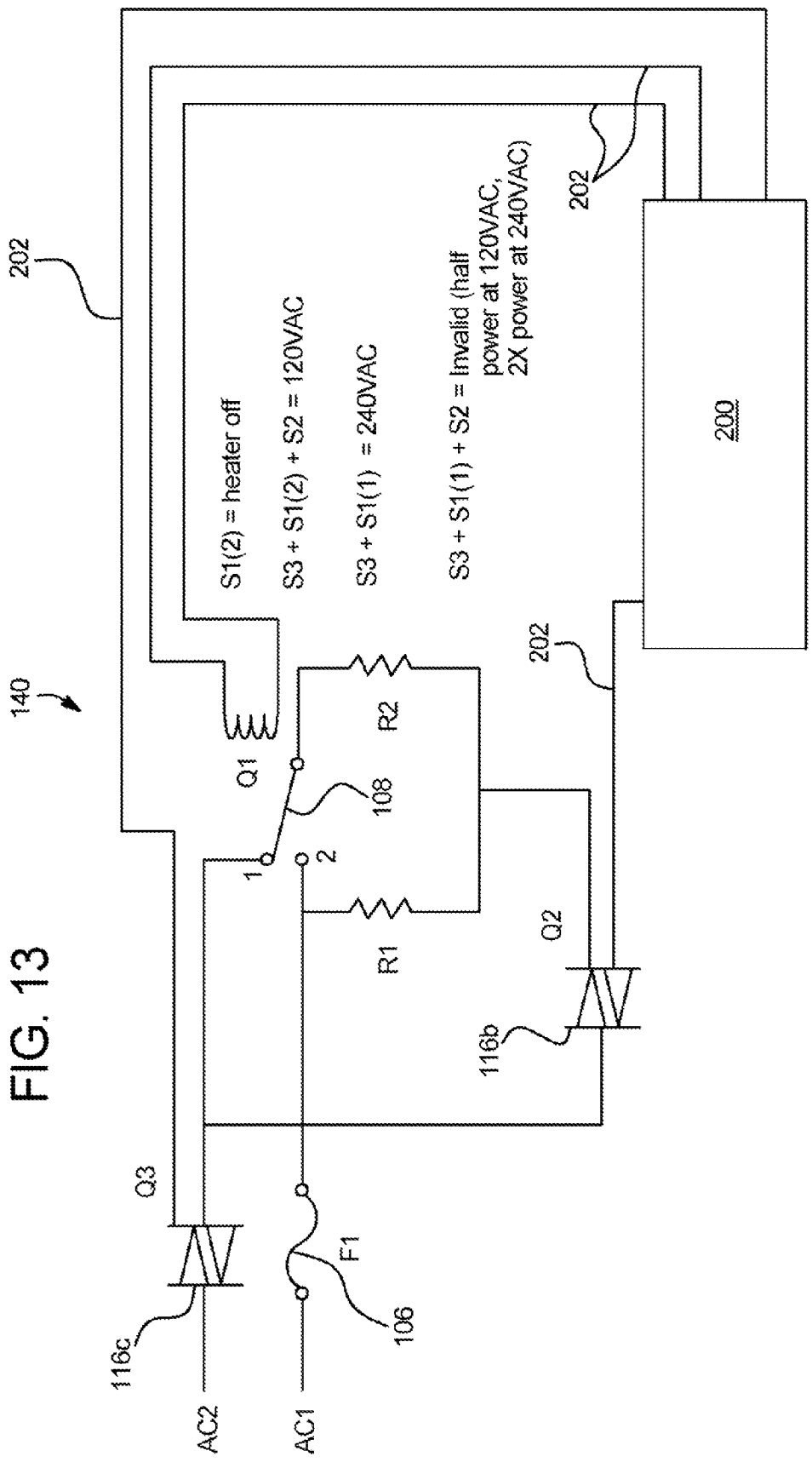

FIG. 13 illustrates a circuit 140, similar to circuit 130, but which includes a variation to minimize the possibility of shorting AC1 and AC2. In FIG. 13, Q1 108 is a mechanical relay, Q2 116b and Q3 116c are solid state relays, e.g., TRIACs as shown. The mechanical configuration of the relay operates to ensure break-before-make operation (contact 1 opens before contact 2 closes and vice versa) to prevent an AC1 to AC2 short circuit. Even with this type of relay, contact arcing during switching will occur if switching a load and can provide a short circuit path via the conductive arc if the arc persists for the time it takes for the relay to completely switch. One way to prevent this occurrence is to prevent arcing. Control circuit 200 can be configured to ensure that TRIAC 116c is open (not conducting) whenever the mechanical relay 108 is changing state to ensure the relay never switches under load.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid heating system for operating with different supply voltages comprising:
   first and second heater elements;
   first and second switching devices connected electrically to the first and second heating elements;
   first and second power lines; and
   a control element configured to provide (i) a first switching device state in which power at a first voltage is supplied via the first and second power lines to both first and second heater elements via both the first and second switching devices and (ii) a second switching device state in which power at a second voltage is supplied via the first and second power lines to the first heater element only via the first switching device.

2. The medical fluid heating system of claim 1, the second switching device in the second state precluding power at the second voltage from being supplied to the second heater element.

3. The medical fluid heating system of claim 1, wherein at least one of: (i) the first voltage is nominally 120 VAC and (ii) the second voltage is nominally 240 VAC.

4. The medical fluid heating system of claim 1, wherein at least one of the first and second switching devices includes a triode for alternating current ("TRIAC") or a reversed paralleled silicon controlled rectifiers ("SCRs").

5. The medical fluid heating system of claim 1, wherein at least one of the first and second power lines includes at least one of: (i) a fuse and (ii) a relay switch.

6. The medical fluid heating system of claim 5, the relay switch controlled by a higher-level system processor.

7. The medical fluid heating system of claim 1, the first and second heater elements a first pair of heater elements, the first and second switching devices a first pair of switching devices, and which includes a second pair of heater elements and a second pair of switching devices connected electrically to the first and second power lines.

8. The medical fluid heating system of claim 7, the second pair of switching devices controlled by the control element.

9. The medical fluid heating system of claim 1, wherein the control element includes a microprocessor, the system further including a voltage detect circuit operable to detect the first or second voltage from the first and second power lines and send a corresponding signal to the microprocessor.

10. The medical fluid heating system of claim 9, the microprocessor including an analog to digital converter ("ADC"), the signal sent from the voltage detect circuit to the ADC of the microprocessor.

11. The medical fluid heating system of claim 9, which further includes a zero cross detect circuit operable with the microprocessor, the microprocessor configured to wait until the zero cross detect circuit indicates that the first or second voltage has crossed zero before the microprocessor causes one of the first or second switching device states to occur.

12. The medical fluid heating system of claim 9, which further includes an alternating current to direct current power supply, which supplies direct current power to at least one of the microprocessor and the voltage detect circuit.

13. The medical fluid heating system of claim 1, the control element communicating with a higher level microprocessor via at least one optical isolator or isolation transformer.

14. A medical fluid heating system for operating with different supply voltages comprising:
first and second heating elements; and
first and second switching devices connected electrically to the first and second heating elements, wherein the first heating element is powered via the first switching device at a first operating voltage, a resistance of the first heating element configured such that the first heating element provides a maximum heating power output at the first operating voltage, and wherein the first and second heating elements are powered in parallel via the first and second switching devices at a second nominal operating voltage, a resistance of the second heating element configured such that the first and second heating elements in parallel provide at least substantially the same maximum heating power output at the second nominal operating voltage.

15. The medical fluid heating system of claim 14, which includes a control element configured to operate the first and second switching devices at the first and second nominal operating voltages.

16. A medical fluid heating system for operating with different supply voltages comprising:
first and second heating elements, the first heating element having a first resistance which is a multiple of a second resistance of the second heating element; and
a control scheme in which the first heating element is powered at a first operating voltage and the first and second heating elements are powered at a second operating voltage.

17. The medical fluid heating system of claim 16, wherein the first resistance is at least approximately three times the second resistance.

18. The medical fluid heating system of claim 16, wherein first operating voltage is 240 VAC and the second operating voltage is 120 VAC.

19. The medical fluid heating system of claim 16, which includes a control element configured to implement the control scheme.

20. The medical fluid heating system of claim 16, which includes a plurality of switching devices operable to implement the control scheme.

* * * * *

UNITED STATES PATENT AND TRADEMARK OFFICE
CERTIFICATE OF CORRECTION

PATENT NO.        : 8,027,572 B2
APPLICATION NO.   : 12/035991
DATED             : September 27, 2011
INVENTOR(S)       : Bedingfield et al.

It is certified that error appears in the above-identified patent and that said Letters Patent is hereby corrected as shown below:

In the Specification:

Column 16, line 49, replace "P=V12/Rp" with --$P=V1^2/Rp$--;

Column 16, line 50, replace "P=V22/R1" with --$P=V2^2/R1$--;

Column 16, line 54, replace "V12/Rp=V22/R1" with --$V1^2/Rp=V2^2/R1$--;

Column 16, line 55, replace "V12/Rp=(2V1)2/R1" with --$V1^2/Rp=(2V1)^2/R1$--;

Column 16, line 58, replace "(2V1)2/V12=R1/Rp" with --$(2V1)^2/V1^2=R1/Rp$--;

Column 16, line 60, replace "R1/Rp=4V12/V12" with --$R1/Rp=4V1^2/V1^2$--; and

Column 16, line 60, replace "V12" with --$V1^2$--.

Signed and Sealed this
Eighteenth Day of February, 2014

Michelle K. Lee
*Deputy Director of the United States Patent and Trademark Office*